United States Patent [19]
Utterberg

[11] Patent Number: 5,895,368
[45] Date of Patent: Apr. 20, 1999

[54] BLOOD SET PRIMING METHOD AND APPARATUS

[75] Inventor: David S. Utterberg, Seattle, Wash.

[73] Assignee: Medisystems Technology Corporation, Las Vegas, Nev.

[21] Appl. No.: 08/717,849

[22] Filed: Sep. 23, 1996

[51] Int. Cl.$^6$ .................................................. A61M 37/00
[52] U.S. Cl. .................... 604/4; 604/80; 604/5; 210/646
[58] Field of Search .................... 604/80–85, 4–6; 210/645, 646

[56] References Cited

U.S. PATENT DOCUMENTS 5,330,425  7/1994  Utterberg .
5,520,640  5/1996  Utterberg .

OTHER PUBLICATIONS

A product Sheet (D3–4361/9711) by Medisystems Corporation, Issue Date: Mar., 1993.

*Primary Examiner*—John G. Weiss
*Assistant Examiner*—Ki Yong O
*Attorney, Agent, or Firm*—Gerstman, Ellis & McMillin, Ltd.

[57] ABSTRACT

An extracorporeal blood set may be primed with physiological solution for use in a blood transporting process such as hemodialysis. The set comprises tubing having a patient connector on an end thereof, and a first branch tube in connection with a source of the solution. The branch tube connects with the set between the ends of the set. The branch tube also connects with further branch tubing, having a second connector which is capable of sealing connection with the patient connector. The method comprises the steps of connecting the patient connector and the second connector to form a closed loop of tubing. One then passes the solution from the source in flow through the first branch tube and further branch tubing to fill them and the set tubing with the solution. One then disconnects the patient connector for subsequent connection with the vascular system of a patient.

10 Claims, 4 Drawing Sheets

BLOOD SET PRIMING METHOD AND APPARATUS

BACKGROUND OF THE INVENTION

Tubular sets are commonly used for conveying blood between a patient and extracorporeal blood treatment apparatus such as dialyzers, blood oxygenators, and similar devices. In the setup of these devices, they must be initially filled with a physiological solution such as normal saline solution before blood is introduced into the sets and extracorporeal treatment apparatus.

Separate or attached priming sets are used in the prior art to deliver such solutions to the fluid pathways of extracorporeal tube sets and the blood processing devices before, during, and after a medical procedure such as hemodialysis. Before the procedure, saline solution must be used to prime the set's fluid pathway, displacing all air. During dialysis, saline solution may have to be rapidly added via the set if the patient suffers hypotension. Also, saline solution may be used as a diluent in drug administration which is directly infused into the extracorporeal blood pathway. Then, at the end of dialysis, saline solution is added to the set to displace all blood back to the patient.

Priming sets are basically simplified versions of the conventional i.v. administration sets used in infusion therapy.

A dialysis set comprises a tubular structure having one end connected to a patient connector and the other end connected to the extracorporeal treatment device. Arterial dialysis sets receive blood from the patient and convey it to the extracorporeal device. Venous sets receive blood from the extracorporeal device and convey it back to the patient.

Such a prior art dialysis extracorporeal treatment system comprises an arterial set and a venous set, both of which are connected to a dialyzer. The arterial set also carries a branching tube, called a saline administration branch line, typically terminating with a luer lock connector for connection with an end of the priming set. Thus, the priming set connects with the saline administration branch line of the arterial set, and saline solution may pass in one step upstream in the arterial set to the patient connector end, to fill that area. Then, in another step, clamps are closed and opened to allow saline to pass downstream through the rest of the set, to prime the rest of the entire system.

As another option in the prior art, the priming set, reversibly connected to a bag of physiological solution, is directly connected to the patient connector of the arterial set. Then, the saline can flow in a single step through the entire system of the arterial set, the dialyzer, and the venous set, to prime it. Following this, one must disconnect the patient connector and priming set, and connect the connector of the priming set to the saline administration branch line, since saline solution will be subsequently needed during the dialysis process.

Since connection of the patient connector with the patient is essentially the last step to be performed after priming and before the initiation of the hemodialysis, the wet patient connector in this circumstance may lie around in an exposed manner, waiting for the final priming steps to be performed, particularly the connection of the priming set to the saline administration branch line, and other final steps. This is undesirable, since it leaves the patient connector both wet from its prior connection, and exposed to the air, which invites contamination.

Also, in the prior art, the use of a separate, separable priming set is generally required to enable the multiple connections and disconnections which are commonly used. However, this causes extra expense in connectors, clamps, sterility protectors, and assembly and packaging.

Further in the prior art, a branching injection site is generally provided to the priming set, which becomes a way that drugs and supplemental fluids may be administered to the system. However, an injection site uses a hypodermic needle to obtain connection through it. The flow through such a needle, and also through valved ports, blunt, hollow probes, and the like used as substitutes for needles, is low because needles and the like are constricted, and thus have low flow rates. The flow is particularly not sufficient for high flow needs such as hypotensive fluid replacement or efficient priming/rinse back of the blood line set. Likewise, valved ports have this disadvantage, and also they are much more expensive than injection sites and needles.

Also, in the circumstance where priming is performed directly through the saline administration branch lines of conventional arterial sets, the retrograde flow of fluid back to the arterial patient connector adds time-consuming connections and clamping.

By this invention, a simplification of the priming process is achieved. The system may be primed in a single step from the patient connector, which is advantageous, and the patient connector may simultaneously be protected from contamination until it is fully time to switch the patient connector to engage the blood system of the patient, to effect the extracorporeal blood treatment process. Where in the prior art two connections after priming must be made, one with the patient connector, and the other with the priming set connector and the saline administration branch line of the set, only one connection after priming has to be made in this invention, that of the patient connector. Also, an extra connector becomes available in accordance with this invention which is a higher flow luer connector, rather than a restricted flow needle or an expensive substitute, so that in the event of the urgent need for high flow fluid administration into the set the access is available.

DESCRIPTION OF THE INVENTION

In accordance with this invention, a method is provided of priming an extracorporeal blood set such as a dialysis set, typically connected to an entire dialysis flow system, to fill it with physiological solution. The set comprises tubing having a patient connector on one end thereof, and a branch tube in connection with a source of the physiological solution. The branch tube connects with the blood set between ends of the blood set.

By this invention, the branch tube connects with further branch tubing having a second connector, which is capable of sealing connection with the patient connector. Preferably, each of the patient connector and the second connector has a minimum flow-through bore diameter of at least two millimeters, which is substantially larger than the bore diameter of needles which are used with injection sites in conventional medical sets. Thus, a relatively high flow rate is possible through these connectors.

Various known connectors exhibit a minimum flow-through bore diameter of at least two millimeters, i.e. there is no constriction of the fluid flow path through the connector of less than two millimeters diameter. The most common are the luer or luer lock connectors, which are preferably used in this invention, and are commonly used throughout the medical field. However, any other connector which fits the requirements and has a flow-through bore diameter of at least two millimeters may be used, for example, screw connectors, bayonet connectors with abutting tubular ends, connectors similar to the Sarns Quick Click connector, clam shell connectors for abutting flanged-end tubing together, and the like. What is excluded are normal medical needle-type connectors, certain valved ports which fail to have an adequate flow path diameter, blunt, hollow probes that extend through slit, elastomeric diaphragms, and the like, unless they are somehow designed to have a flow path which is at least two millimeters in diameter throughout its length.

Thus, the method of this invention comprises the steps of: connecting the patient connector and the second connector to form a closed loop of tubing. One then passes the solution from its source in flow through the branch tube and the further branch tubing, to fill them and the set tubing with the solution. One then disconnects the patient connector for subsequent connection with a vascular system of a patient. This subsequent connection can be immediate, so that the patient connector is not subject to contamination by spending time exposed to the air. Typically, the patient connector is a conventional male luer lock connector, while the second connector is a conventional female luer lock connector.

It is preferred to practice the method with the further step of blocking (occluding) flow through the branch tube at a first point, which is positioned on the branch tubing between the further branch tubing and the set tubing. The effect of this is to temporarily cause all of the solution flow from the solution source to pass through the further branch tubing, and through the patient connector, and then through the set tubing from the end thereof, so that the priming of the entire system can proceed from one end to the other without any need for a less desirable retrograde flow step.

After this, one then can block or occlude flow through a second point on the further branch tubing, and one can simultaneously open flow through the first point in the first branch tube, typically after the set tubing is filled with the solution. Thus, saline flow can now pass directly to the set through the first branch tube if and when needed.

During the extracorporeal blood treatment procedure, one can subsequently connect a third connector, typically a luer connector, to the second connector of the further branch tubing. This third connector typically also has a minimum flow-through bore diameter of at least two millimeters, and can communicate with another source of physiological solution, for example, a drug-containing solution for medicating the patient directly through the set, or added saline in the event of a hypotensive episode. Since the connection of the second and third connectors is preferably a luer connection or the equivalent, rather than a connection through a needle-penetrable injection site or equivalent structures, a much greater flow of solution is available to the patient, which may be lifesaving in the event of a hypotensive episode. Typical branched injection sites which use a needle, or a corresponding, blunt tube, exhibit constricted flow characteristics compared with luer connector systems, since the needle or blunt equivalent must be thin enough to sealingly penetrate through a resilient wall of some kind in an injection site. Thus, significant improvements are achieved by providing the second connector, which is in branching connection with the first branch tubing, providing added capacity for high flow fluid administration to the patient through the set in the event of an emergency, for example a flow of at least 300 ml. per min.

At the end of the extracorporeal blood procedure, one may perform the step of subsequently reconnecting the patient connector and the second connector. More physiological solution may then be passed from the source of solution in flow through the branch tube and further branch tubing, to flush the set tubing with said solution beginning at the patient connector end, through the entire length of the set tubing, and also typically including the dialyzer or other extracorporeal treatment device and the venous set tubing as well.

Thus, the change from the prior art, which comprises the addition of further branch tubing and a second connector as a substitute for a branching injection site of the prior art, provides the above significant opportunities and advantages. By this invention, infusions through the saline administration branch of blood sets provide greater flow capacities, when compared with injection sites and needles, and their blunt equivalents and valved female connectors. Such high flow infusions are particularly necessary in emergency situations, and may be lifesaving. Also blood line priming of the arterial set may be accomplished without removing the priming set from sterile connection with the blood line.

In a preferred embodiment, the priming set may be integrally attached to the blood line so that the user does not have to make any connection there. Such an integral connection results in decreased parts, allowing significant cost savings. Similarly, blood line rinseback may take place without removing the priming set from its sterile connection with the blood line.

DESCRIPTION OF SPECIFIC EMBODIMENTS

Figure 1:
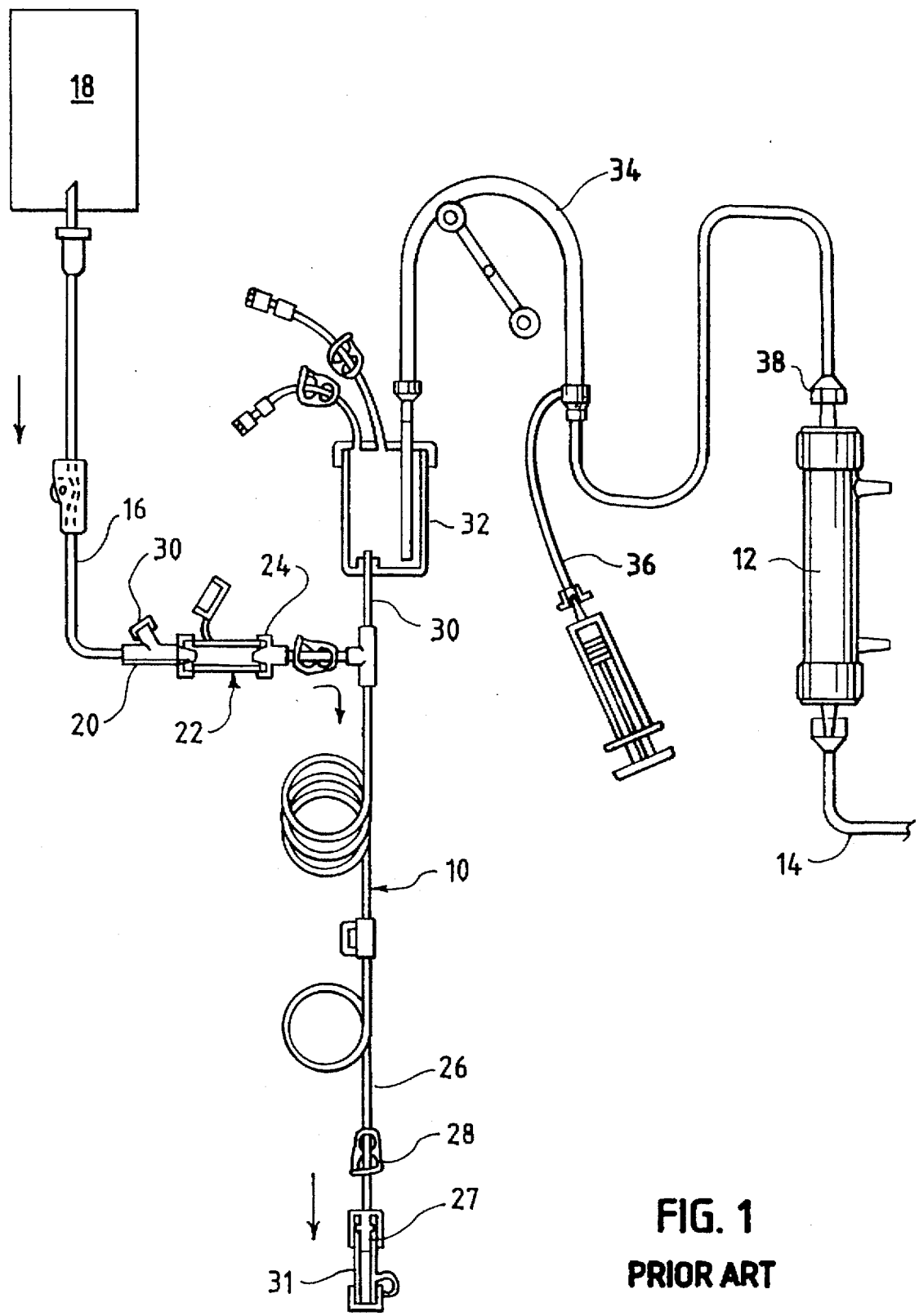
FIG. 1 is view of a dialysis set of the prior art showing a dialysis set being primed while connected to a dialyzer.

Referring to FIG. 1, an arterial set 10 of the prior art for hemodialysis is shown, being connected with a conventional hemodialyzer 12 which, in turn, is connected to a conventional venous blood flow set 14.

For priming, a priming set 16 connects at one end thereof to the bag 18 of normal saline solution, and connects at its other end 20 through circulation/priming connector 22, to a branch connector 24 of set 10. In one embodiment of the prior art, both connectors 20 and 24 are male luer connectors, so that priming connector 22 is required to receive both of them in sealed, connected, relation.

Saline solution passes from bag 18 through priming connector 16, first downwardly through proximal tubing portion 26 to fill the upstream portion of arterial set 10 extending to patient connector 27. Then, clamp 28 can be closed, so that subsequent flow goes through distal portion 30 of the set, which in this embodiment contains a bubble trap 32, roller pump tubing 34, and a branching heparin line 36. Set 10 conventionally connects at its opposite end 38 to dialyzer 12. Venous set 14 leads to a second patient connector like connector 27, both of which are conventionally connected through a fistula or the like to the blood stream of the patient to provide a blood circuit.

It should be noted that the luer connector 20 of prior art priming set 16 carries a branching injection site 30 which may be accessed by a needle, or if desired by a blunt, hollow spike or a valved port with respect to newer technology.

However, in all of these circumstances, flow into the system through access port 30 is substantially constricted when compared with the typical luer-type connector which is currently used in medical devices.

If desired, to avoid the two step priming of flow first in one direction through tubing section 26, and then in the other direction through tubing section 30, one can directly connect set 16 through its connector 20, and a connector 31 similar to connector 22, with patient connector 27, so that the entire system can be primed with a single flow step, the saline passing through patient connector 27 and then through the entire length of the set, and through dialyzer 12 and venous set 14 as well. However, prior to beginning dialysis, one must then disconnect the respective connectors 20, 27 and reconnect connector 20 with branch connector 24. This leaves patient connector 27 wet from use and exposed to the air for a period of time before the final connection to the patient fistula needle set is made and the dialysis procedure begins with flowing blood through the sets. This raises the risk of problems with contamination.

Figure 2:
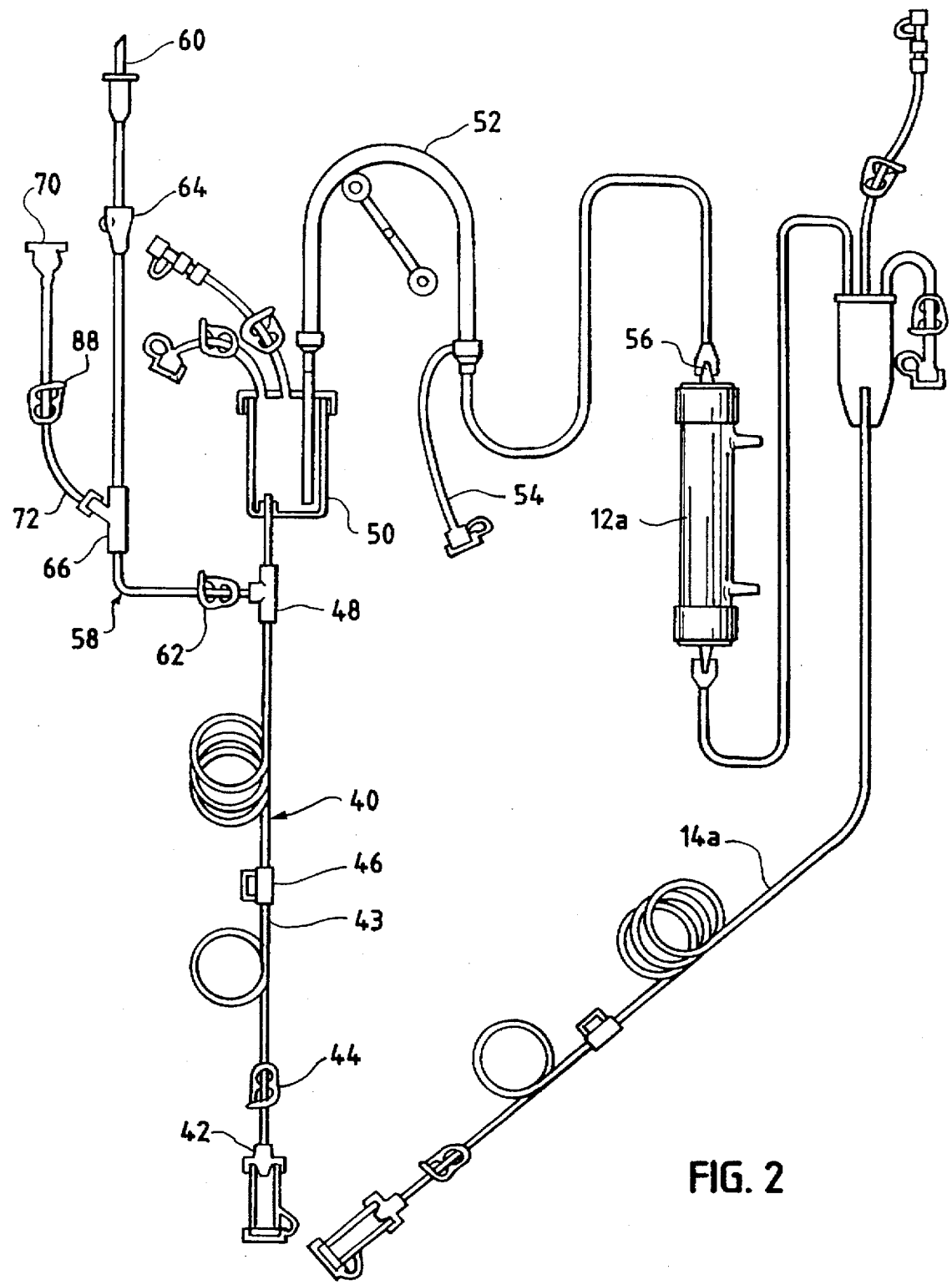
FIG. 2 is a view of a dialysis set in accordance with this invention, connected to a dialyzer and another set to form a dialysis flow system.

Referring to FIG. 2, the blood flow path for a dialysis setup is shown, being similar to that of the prior art, except for that which is otherwise described herein.

As before, an arterial set 40 is shown, being connected to a dialyzer 12a and from there to a venous set 14a. The latter two items are typically unchanged from the prior art. Arterial set 40 defines a patient connector 42, and a length of tubing 43 which carries various elements such as clamp 44, injection site 46, T-connector 48, gas trap 50, roller pump tubing 52, branching heparin line 54, and distal end connector 56, for connection with dialyzer 12a. All of these items may be of conventional construction.

T-connector 48 carries a branching tube 58 which, in accordance with this invention, may comprise an integrally and permanently attached set for connecting at its remote end 60 to a conventional source of saline or other physiological solution. Branching solution set 58 may carry flow clamp 62 and roller clamp 64 for control of solution flow. Also, branching tube 58 may carry a Y or T member 66, to which is connected further branch tubing 72, which is terminated with a female luer lock connector 70. On-off clamp 88 is also provided to the further branch tubing 72.

Basically, a chief difference of this set over the prior art is that where the set of the prior art, and particularly the connected priming set, has a branching injection site having a resilient, penetrable wall through which fluid flow connection is made by a needle or equivalent, by this invention, branch tubing 58 carries a further branch tubing 68, which terminates with a luer lock connector 70 having the advantage of higher flow characteristics because it has a flow-through bore diameter greater than two millimeters.

Figure 3:
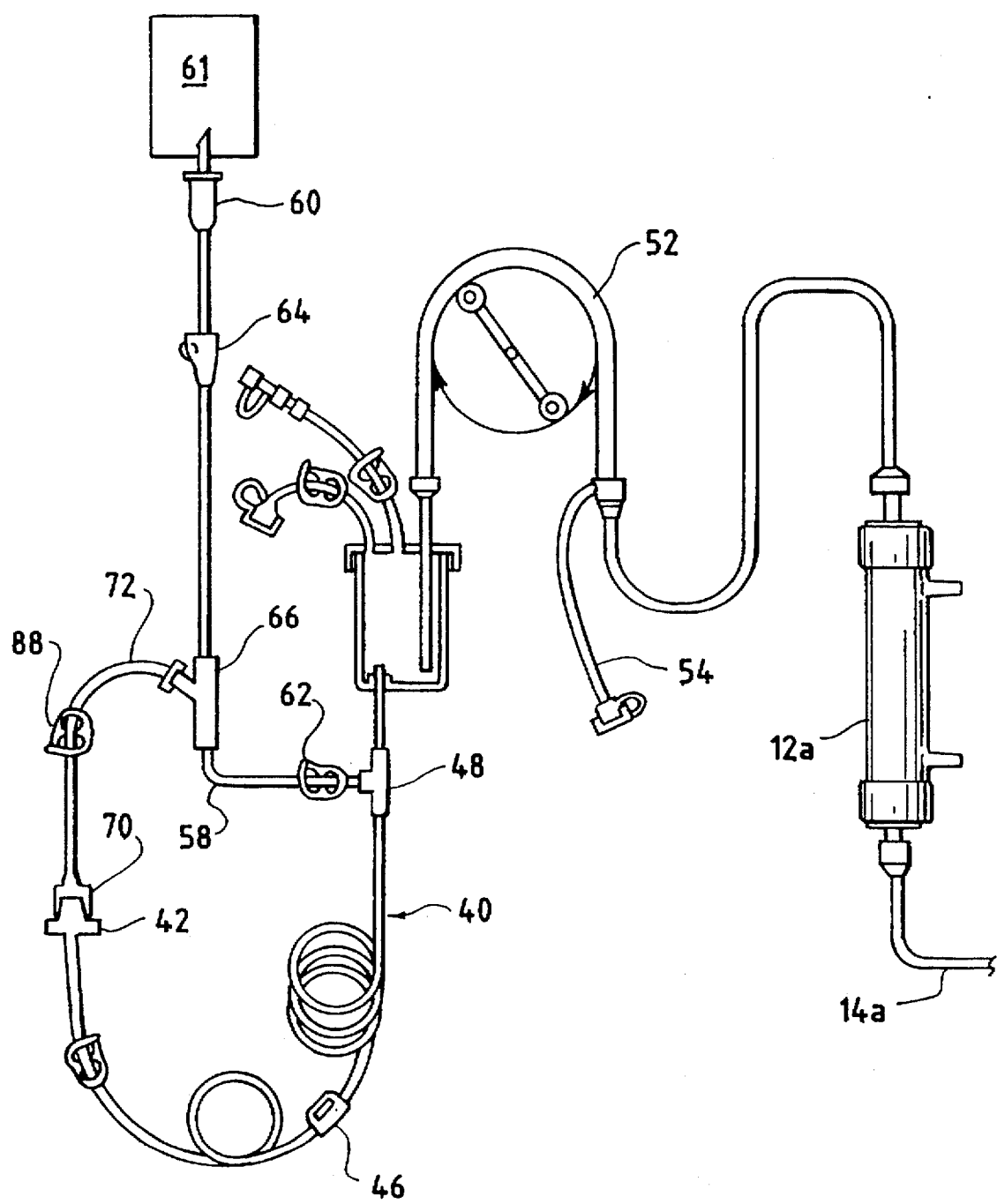
FIG. 3 is a view of the set of FIG. 2 in the process of being primed.

As shown in FIG. 3, it becomes possible to prime the set in a simpler and safer manner, as shown. Patient connector 42, which is generally a male luer lock connector, is brought into connecting relation with the second connector 70 of the further branch line 72, so that a portion of the set 40 forms a closed loop as shown, comprising a proximal portion of set 40. The loop extends from patient connector 42 counterclockwise around to T-connector 48, from there extending along branch tube 58 to Y-connector 66. From there the loop closes with further branch tubing 72, to form a complete loop with the connection of members 42, 70.

To prime the set, typically, on-off clamp 62 is closed, and flow from saline container 61 is released by the opening of roller clamp 64, so that saline passes from bag 61 to Y-connector 66, and from there through further branch tubing 72 and patient connector 42 into the proximal end of set 40. From there, solution can pass through the entire set 40, through dialyzer 12a, and through venous set 14a, to fill the system. As can be seen, this is a one step process, which avoids the need for the two-directional flow filling steps which would be the case if the solution came in at T-connector 48.

By way of advantage, only a single connection and disconnection needs to be made on arterial set 40 after priming, and that is the connection of patient connector 42 to the patient's fistula. Until that time, patient connector 42 can stay in its connection with second connector 70, to prevent exposure of the wet connector 42 to possible contamination, contrary to the prior art.

The branch set 58 is in this embodiment an integral set, so that no separate set connection is required, except for the single connection of connector into solution bag 61. Thus, a significant cost saving can be made due to the absence of any need for connecting a priming set into the system since it is already integrally present. Thus, extra expense for the necessary connectors, sterility protectors, assembly, and separate packaging of the priming set is avoided.

During dialysis, if there is a need to put additional solution into the system, the female luer connector 70 of the further branch tubing 72 is available for the purpose. For example, drug-containing solutions may be added to the system, or an added unit of saline solution may be connected and administered with high flow, so that two bags of saline solution may be thus administered simultaneously and at high flow in response to an emergency, such as may result from a serious hypotensive episode. To the contrary, in the prior art, only a relatively low fluid flow can be administered through an injection site which is replaced in this invention by further branch tubing 72 and female luer connector 70.

Figure 4:
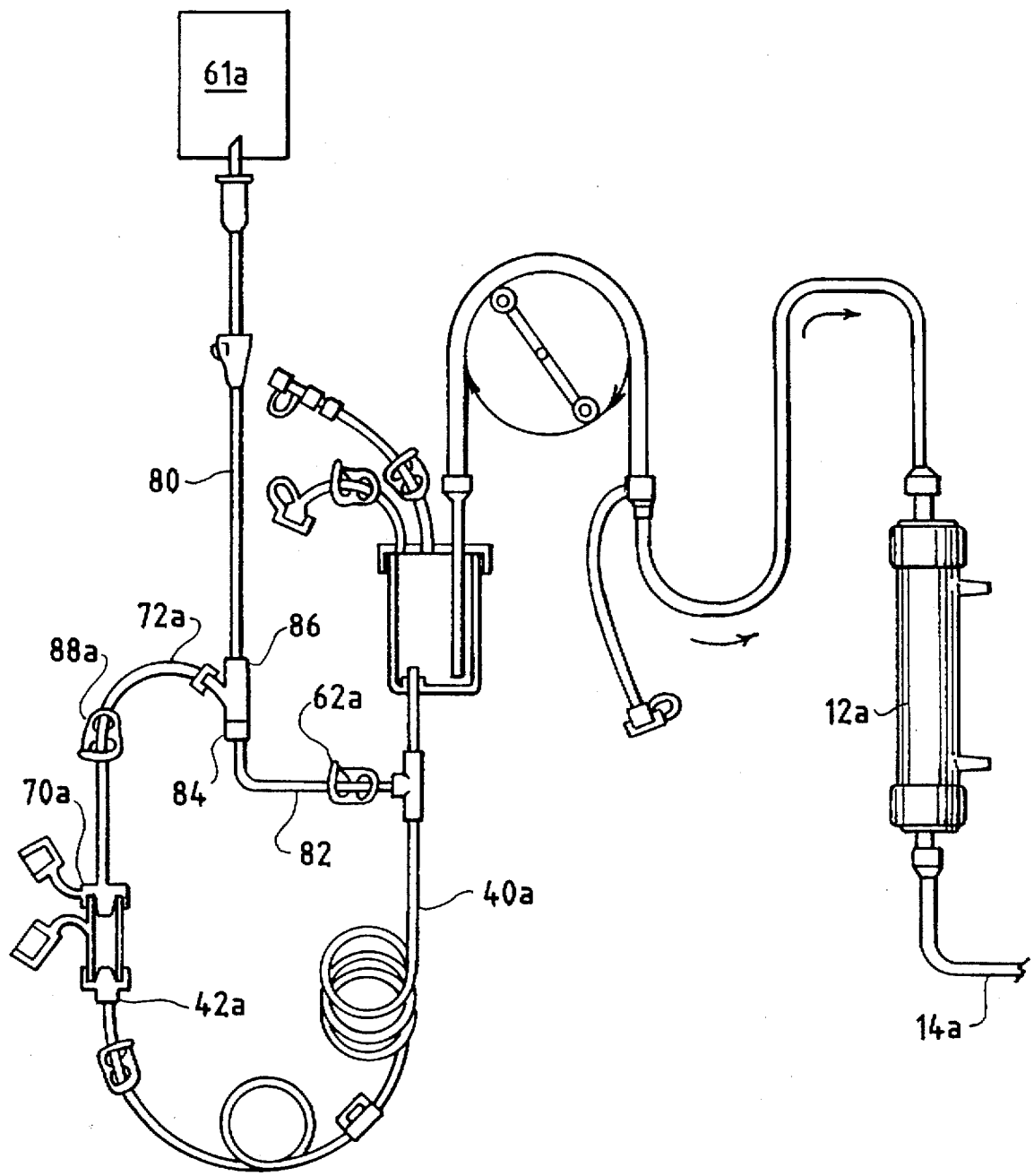
FIG. 4 is a view of an alternative set in accordance with this invention in the process of being primed.

Referring to FIG. 4, a similar system to FIGS. 2–3 is disclosed, except that the priming set 80 used is not integral with set 40a. Instead, set 40a carries a conventional branch tubing 82 and a luer connector 84. Priming set 80 defines a forward connector 86 having a Y-connection, to which the further branch tubing 72a and its female luer connector 70a are attached.

As in the previous embodiment, patient connector 42a can connect with second connector 70a, to form a loop in the set system as priming takes place, with priming desirably taking place through connector 42a at the end of the set, for the purpose of avoiding the two step, two flow direction priming system, while at the same time requiring only one disconnection and connection after priming, namely that of patient connector 42a which can be immediately connected to the patient's fistula.

Thus, the setup of dialysis can take place with improved convenience and facility.

During the dialysis procedure, as previously stated, further branch line 72a, with its luer connector 70a, is available for connection to a third connector of another source of fluid for rapid administration, if needed, to the patient.

At the end of dialysis, in both the systems of FIGS. 3 and 4, one can separate the respective patient connectors 42, 42a, from the patient's fistula, and reconnect them respectively to the second connectors 70, 70a. This provides a source of solution from bags 61, 61a (with clamps 62, 62a being closed) so that the dialysis system may be flushed with saline solution through the entire set 40a, as well as through dialyzer 12a and venous set 14a, thus returning essentially all of the blood back to the patient by means of the patient connector of venous set 40a.

During normal operation, clamps 88, 88a of further branch tubings 72, 72a may be closed, so that the solution flow line is directly from bag 61, 61a through the branch tubing 58, 80 to the main set tubing 40, 40a.

The above has been offered for illustrative purposes only, and is not intended to limit the scope of the invention of this application, which is as defined in the claims below.

That which is claimed:

1. The method of priming an extracorporeal blood set with physiological solution for use in a blood transporting process, which set comprises tubing having a patient connector on an end thereof, and a first branch tube in connection with a source of said solution, said branch tube connecting with said set between ends thereof;

said branch tube connecting with further branch tubing having a second connector capable of sealing connection with said patient connector, each of said connectors having a minimum flow-through bore diameter of at least 2 mm.;

said method comprising the steps of: connecting the patient connector and the second connector to form a closed loop of tubing; passing said solution from said source in flow through said first branch tube and further branch tubing to fill them and said set tubing with said solution; and disconnecting said patient connector for subsequent connection with the vascular system of a patient.

2. The method of claim 1, further comprising the step of occluding flow through said first branch tube at a first point between said further branch tubing and said set tubing, to temporarily cause all of said solution flow from said solution source to pass through said further branch tubing, said patient connector, and then through said set tubing.

3. The method of claim 2 further comprising the step of occluding flow through a second point on said further branch tubing and opening flow through said first point, after said set tubing is filled with said solution.

4. The method of claim 1 further including the step of subsequently connecting a third connector to said second connector, said third connector having a minimum flow-through bore diameter of at least 2 mm. and communicating with another source of physiological solution, and also causing flow of said solution through said branch tubing into said set tubing.

5. The method of claim 1 further including the step of subsequently passing a bolus of said physiological solution through said further branch tubing at a maximum practicable flow rate into said set tubing.

6. The method of claim 1 further including the step of subsequently reconnecting said patient connector and said second connector, and again passing said physiological solution from said source in flow through said branch tube and further branch tubing to flush said set tubing with said solution.

7. The method of priming an extracorporeal blood set with physiological solution for use in a dialysis process, which set comprises tubing having a patient connector on the end thereof, and a first branch tube in connection with a source of said solution, said branch tube connecting with said set between ends thereof, said branch tube connecting with a further branch tubing having a second connector capable of sealing connection with said patient connector, each of said connectors having a minimum flow-through bore diameter of at least 2 mm;

said method comprising the steps of: connecting the patient connector and the second connector to form a closed loop of tubing; passing said solution from said source in flow through said first branch tube and further branch tubing to fill them and said set tubing with said solution, and further comprising the step of occluding flow through said first branch tube at a first point between said further branch tubing and said set tubing, to temporarily cause all of said solution flow from said solution source to pass through said further branch tubing, said patient connector, and then through said set tubing; and disconnecting said patient connector for subsequent connection with the vascular system of a patient; and further including the step of subsequently reconnecting the patient connector and said second connector, and again passing said physiological solution from said source in flow through said branch tube and further branch tubing to flush said set tubing with said solution.

8. The method of claim 7 further comprising the step of occluding flow through a second point on said further branch tubing and opening flow through said first point, after said set tubing is filled with said solution.

9. The method of claim 8 further including the step of subsequently passing a bolus of said physiological solution through said further branch tubing at a maximum practicable flow rate into said set tubing.

10. The method of claim 9 further including the step of subsequently connecting a third connector to said second connector, said third connector having a minimum flow-through bore diameter of at least 2 mm. and communicating with another source of physiological solution, and causing flow of said solution into said branch tubing and into said set tubing.

* * * * *